United States Patent [19]

Ward

[11] 4,332,822
[45] Jun. 1, 1982

[54] GUANIDINE DERIVATIVES

[75] Inventor: Terence J. Ward, Slough, England

[73] Assignee: John Wyeth & Brother Limited, Maidenhead, England

[21] Appl. No.: 229,902

[22] Filed: Jan. 30, 1981

[30] Foreign Application Priority Data

Feb. 5, 1980 [GB] United Kingdom ............... 8003848

[51] Int. Cl.³ ............... C07C 125/08; C07D 207/30; A61K 31/40; A61K 31/165

[52] U.S. Cl. ............... 424/324; 424/251; 424/273 R; 424/274; 544/331; 544/332; 548/315; 548/316; 564/104; 548/544; 548/546; 548/557; 548/558; 548/550; 548/561

[58] Field of Search ............... 564/104; 260/326.43; 544/331, 332; 548/315, 316; 424/251, 273 R, 274, 324

[56] References Cited

U.S. PATENT DOCUMENTS

| | | | |
|---|---|---|---|
| 3,632,645 | 1/1972 | Bream et al. | 260/453.5 |
| 3,634,508 | 1/1972 | Bream et al. | 564/182 |
| 3,822,262 | 7/1974 | Bream et al. | 544/332 |
| 4,140,793 | 2/1979 | Ward | 424/274 |
| 4,265,905 | 5/1981 | Shen et al. | 424/304 |

OTHER PUBLICATIONS

Adams et al., J. Org. Chem. 17, pp. 1162–1171 (1952).
Scholtysik et al., Arzneim. Forsch. 25, pp. 1483–1491 (1975).

Primary Examiner—Dolph H. Torrence
Attorney, Agent, or Firm—Richard K. Jackson

[57] ABSTRACT

Novel cyanoguanidine derivatives having the formula

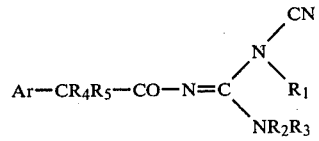

wherein Ar is a phenyl or pyrrol-1-yl group substituted by one or more substituents selected from halogen, trifluoromethyl, lower alkyl, lower alkoxy and nitro and $R_1$, $R_2$, $R_3$, $R_4$ and $R_5$ are each independently hydrogen or lower alkyl or $R_1$ and $R_2$ taken together form dimethylene or trimethylene, lower blood pressure and, in some cases are also anti-ulcer agents.

8 Claims, No Drawings

GUANIDINE DERIVATIVES

This invention relates to novel guanidine derivatives, to processes for their preparation and to pharmaceutical compositions containing them.

The novel guanidine derivatives provided by the invention are compounds having the general formula I

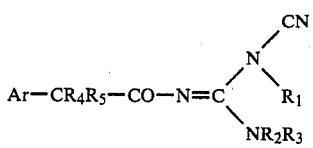

wherein $R_1$ and $R_2$ independently represent hydrogen or lower alkyl or $R_1$ and $R_2$ taken together represent —$(CH_2)_n$— where n is 2 or 3; $R_3$, $R_4$ and $R_5$ independently represent hydrogen or lower alkyl; and Ar represents a phenyl or pyrrol-1-yl group substituted by at least one substituent selected from halogen, trifluoromethyl, lower alkyl, lower alkoxy and nitro. Preferably at least one of the ortho-position carbon atoms of the phenyl or pyrrol-1-yl group is substituted, advantageously both such carbon atoms being substituted.

The term "lower" as used herein to refer to alkyl or alkoxy means that the alkyl or alkoxy group contains 1 to 6 carbon atoms. Preferably the group contains 1 to 4 carbon atoms.

$R_1$ and $R_2$ may each represent hydrogen or lower alkyl, for example, methyl, ethyl, propyl or butyl. Alternatively $R_1$ and $R_2$ when taken together may represent dimethylene or trimethylene. In this case $R_3$ preferably represents hydrogen. Thus the group having the formula II

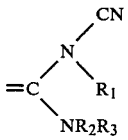

may represent a group having formula (IIIa) or (IIIb).

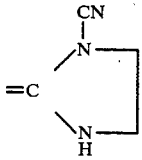

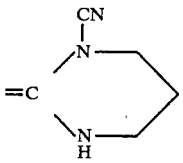

$R_3$, $R_4$, $R_5$ independently represent hydrogen or lower alkyl, for example, methyl, ethyl, propyl or butyl. Advantageously $R_1$, $R_2$, $R_3$, $R_4$ and $R_5$ all represent hydrogen.

Ar represents a phenyl or pyrrol-1-yl group substituted by at least one substituent, preferably two substituents, selected from halogen (for instance chlorine or bromine), trifluoromethyl, lower alkyl (for instance, methyl, ethyl, propyl or butyl), lower alkoxy (for instance, methoxy, ethoxy, propoxy or butoxy) and nitro. As substituents we prefer to employ halogen, lower alkyl and trifluoromethyl. Preferably at least one of the ortho-position carbon atoms of the phenyl or pyrrol-1-yl group is substituted. More preferably, both such carbon atoms are substituted by identical substituents. As examples of Ar there may be particularly mentioned 2,6-dichlorophenyl; 2,6-dimethylphenyl; 2,6-di(trifluoromethyl)phenyl; 2,5-dimethyl-1H-pyrrolyl-1-yl; 2,5-dichloro-1H-pyrrol-1-yl; and 2,5-ditrifluoromethyl-1H-pyrrol-1-yl.

Although the compounds of the invention have been shown above in formula I in terms of the acylimino form it is possible that the compounds exist in other tautomeric forms or mixtures of such forms. For example, possible structures of the compounds where $R_1$, $R_2$, $R_3$, $R_4$ and $R_5$ are all hydrogen include the acylamino structure (IVa)

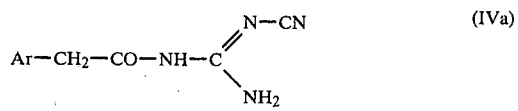

and the enol forms (IVb), (IVc) or (IVd)

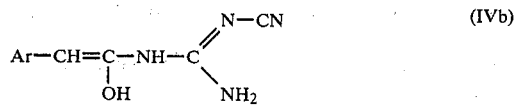

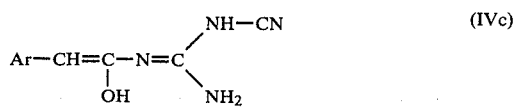

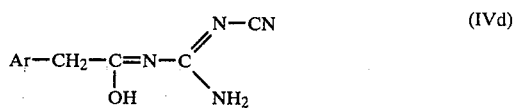

Where in this specification there is used a name or formula referring to any particular tautomeric form of a compound, it is to be understood that the name or formula designates the compound itself irrespective of its tautomeric form.

The novel compounds of the invention can be prepared by a process where (a) a compound having the formula (V)

(wherein $R_1$, $R_2$ and $R_3$ are as defined above) or a reactive derivative thereof (including for example, an alkali metal salt) is acylated by reaction with an acid having the formula (VI)

(wherein $R_4$, $R_5$ and Ar are as defined above) or a reactive derivative thereof; or (b) a compound having the formula (VII)

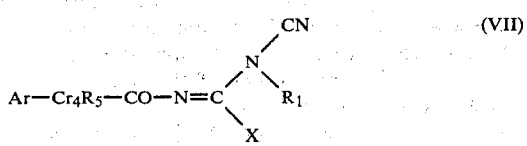

(wherein $R_1$ represents hydrogen or lower alkyl, $R_4$, $R_5$ and Ar are as defined above and X represents a replaceable atom or group, for example, a chlorine atom or lower alkylthio group, preferably a methylthio group) is reacted with a compound having the formula $HNR_2R_3$ (wherein $R_2$ and $R_3$ are independently hydrogen or lower alkyl) or a salt thereof, preferably an alkali metal salt; or (c) a compound having the formula (VIII)

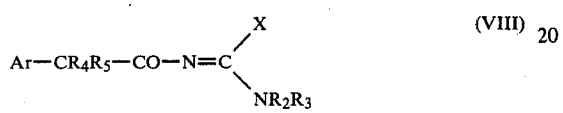

(wherein $R_2$, $R_3$, $R_4$, $R_5$, Ar and X are as defined under process (b) above) is reacted with a compound having the formula $HNR_1CN$ (where $R_1$ is as defined under process (b) above) or a salt thereof, preferably an alkali metal salt; or (d) a compound having the formula X—CN (wherein X is a replaceable atom or group, preferably a bromine atom) is reacted with a compound having the formula (IX)

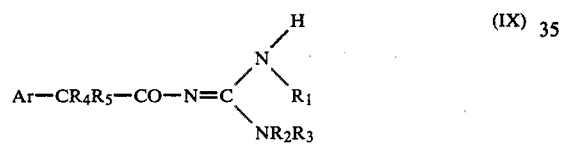

(wherein $R_1$, $R_2$, $R_3$, $R_4$, $R_5$ and Ar are as defined in relation to formula I) or a salt thereof, preferably an alkali metal salt; or (e) a compound having the formula (I), as illustrated and defined above subject to the proviso that at least one of $R_1$, $R_2$ and $R_3$ is hydrogen, or a derivative thereof, for instance an alkali metal salt thereof, is alkylated to introduce a lower alkyl group as $R_1$, $R_2$ or $R_3$.

It will be appreciated by those skilled in the art that a number of starting materials in the aforesaid process have been identified by one possible structure whilst other alternative tautomeric structures are also possible. Thus, as with the novel guanidine derivatives of the invention, names and formulae of starting materials in the process of the invention are intended to designate the compounds irrespective of their tautomeric form.

The starting materials for process (a) are generally known and, where new, are obtainable by known methods. The acylation may be carried in manner known in the art for acylation of amines. As acylating agent there may be used the acid chloride, the simple or mixed anhydrides of the acid or the active esters. The acid itself may be used where the compound to be acylated is in the form of an activated amine, for instance, the phosphazo derivative from a 3-cyano-1,1-di(lower alkyl)guanidine.

The acylation may be carried out in the following manner. The acid chloride is added to a cooled alkaline solution of the compound having formula V. The reaction may proceed instantaneously under such conditions. The acylation product may have a tendency to hydrolytic decomposition under the alkaline conditions. Thus to avoid possible loss of yield, it is recommended to recover the acylation product from the reaction mixture without delay.

Compounds having the formula VII may be prepared in known manner. For instance, an acid-chloride having the formula (X)

may be reacted with a compound having the formula (XI)

to form the compound having formula VII. As compound of formula XI, N-cyano-S-methylisothiourea is preferably employed. The reaction of the compound having formula VII with the amine having formula $HNR_2R_3$ or its salt such as the alkali metal salt may be carried out in known manner for the replacement reaction.

The compounds having formula VIII used as starting materials for process (c) are preferably isothiourea derivatives, symbol X being lower alkylthio, preferably methylthio. The isothiourea derivatives can be prepared by the reaction of the acyl chloride having formula X with a compound having the formula (XII)

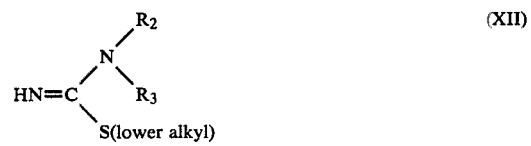

preferably S-methylisothiourea. The reaction of the compound having formula VII with the amine having the formula $HNR_1CN$ or a suitable salt, for instance, an alkali metal salt, can be carried out in known manner for the replacement reaction.

Process (d) may also be carried out in known manner for the replacement reaction. The guanidine derivatives having formula IX used as starting materials can be prepared by acylation of guanidine or its appropriate alkyl substituted derivative with the methyl ester of the acid having formula VI.

Process (e) may be carried out in standard manner for the alkylation of amines. The starting material to be alkylated may be prepared by any one of processes (a) to (d).

The novel guanidine derivatives of the invention possess pharmacological activity. In particular they lower blood pressure. Thus the compounds may be evaluated by testing in standard hypotensive or antihypertensive pharmacological procedures. The compound of Example 1 hereinafter was tested by measuring the systolic pressure of male spontaneously hypertensive rats immediately before administration of the compound and various times thereafter. The results obtained were:

| Compound | Dose Tested (mg/kg) p.o. | Blood Pressure As a Percentage Of Initial Blood Pressure After A Period Of:- | | | |
|---|---|---|---|---|---|
| | | 2 hrs. | 6 hrs. | 24 hrs. | 30 hrs. |
| N-[Amino(cyanamino)methylene]-2,6-dichlorophenylacetamide | 50 | 69.3 | 72.3 | 74.6 | 74.3 |

The anti-hypertensive activity may be of prolonged duration as can be seen in the case of the results above.

Some of the novel guanidine derivatives of the invention are also anti-ulcer agents which possess antisecretory activity in the test of H. Shay, D. Sun and H. Greenstein, Gastroenterology, 1954, 26, 903-13. Compounds which possess anti-secretory activity are exemplified by N-[amino(cyanamino)methylene]-2,6-dichlorophenylacetamide which gave the following results in the test of Shay et al.

| Compound | Dose mg/kg (i-duod.) | % Decrease | | | |
|---|---|---|---|---|---|
| | | Vol. of Gastric Contents | Conc. of Acid | Amount of Free Acid | Total Acid |
| N-[Amino(cyanamino)methylene]-2,6-dichlorophenylacetamide | 30 | 74 | 40 | 77 | 71 |

The invention includes a pharmaceutical composition comprising a novel guanidine derivative provided by the invention in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient (with or without other carriers) is surrounded by the carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. When the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredient; the unit dosage form can be packaged compositions, the package containing specific quantities of compositions, for example, packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg or less to 500 or more, according to the particular need and the activity of the active ingredient. The invention also includes the compounds in the absence of carrier where the compounds are in unit dosage form.

Pharmaceutical compositions containing compounds of the invention possessing antisecretory activity may be administered as anti-ulcer compositions. Those compositions may be administered orally in liquid or solid composition form and such compositions may include one or more antacid ingredients, e.g. aluminium hydroxide, magnesium hydroxide, bismuth carbonate, aluminium glycinate, calcium carbonate, magnesium trisilicate, sodium bicarbonate or the alumina gel described in U.K. Pat. No. 1,284,394.

The following Examples illustrate the invention:

EXAMPLE 1

N-[Amino(cyanamino)methylene]-2,6-dichlorobenzeneacetamide

Potassium hydroxide (1.12 g, 0.02 m) was dissolved in water (4 cm$^3$). Acetone (5 cm$^3$) and dicyandiamide (1.05 g, 0.0125 m) were added and the solution cooled in ice. 2,6-Dichlorobenzeneactyl chloride (2.23 g, 0.01 m) was rapidly added to the stirring cooled solution. After the addition, water (40 cm$^3$) was added and the solution was acidified with glacial acetic acid to give a white precipitate. The precipitate was filtered off, washed well with water and recrystallised from ispropyl alcohol to give the title compound as a white solid (1.26 g), melting point 210°-212° C.

EXAMPLE 2

The following acid chlorides are reacted with the following guanidine derivatives in a similar manner to Example 1 to give the stated products:

| Acid Chloride | Guanidine Derivative | Product |
|---|---|---|
| 2-Nitrobenzene acetyl chloride | cyanoguanidine | N-[Amino(cyanamino)methylene]-2-nitrobenzeneacetamide |

-continued

| Acid Chloride | Guanidine Derivative | Product |
|---|---|---|
| 2,6-Dimethyl-benzeneacetyl chloride | 3-cyano-1,1-dimethyl-guanidine | N-[cyanamino(dimethylamino)methylene]-2,6-dimethylbenzeneacetamide |
| 3,4-Dichloro-benzeneacetyl chloride | 1-cyano-1,3-dimethyl-guanidine | N-[(cyano(methyl)amino)(methylamino)methylene]-3,4-dichlorobenzeneacetamide |
| 2,6-Diethoxy-benzeneacetyl chloride | 1-cyano-3-(2-methyl-propyl)-guanidine | N-[cyanamino(2-methylpropylamino)methylene]-2,6-diethoxybenzeneacetamide |
| 2,5-Dichloro-1H-pyrrole-1-acetyl chloride | cyanoguanidine | N-[Amino(cyanamino)methylene]-2,5-dichloro-1H-pyrrole-1-acetamide |
| α,α-Dimethyl-2,6-di(trifluoromethyl)-benzeneacetyl chloride | cyanoguanidine | N-[Amino(cyanamino)methylene]-α,α-dimethyl-2,6-di(trifluoromethyl)-benzeneacetamide |
| 2,6-Dichloro-benzeneacetyl chloride | 2-imino-1-imidazoline-carbonitrile | 2-[(2,6-dichlorobenzeneacetyl)imino]-1-imidazolinecarbonitrile |
| 2,6-Difluoro-benzeneacetyl chloride | 2-imino-3,4,5,6-tetrahydro-1-[H]-pyrimidine-carbonitrile | 2-[(2,6-difluorobenzeneacetyl)imino]-3,4,5,6-tetrahydro-1-[1H]-pyrimidinecarbonitrile |

I claim:

1. A compound having the formula

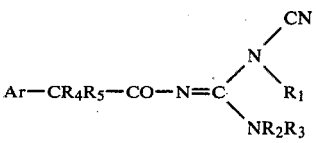

wherein $R_1$ and $R_2$ are independently selected from hydrogen and lower alkyl or $R_1$ or $R_2$ taken together represent $-(CH_2)_n-$ where n is selected from 2 and 3; $R_3$, $R_4$ and $R_5$ are independently selected from hydrogen and lower alkyl; and Ar is selected from phenyl and pyrrol-1-yl groups that are substituted by one to two substituents, each substituent being independently selected from halogen, trifluoromethyl, lower alkyl, lower alkoxy and nitro.

2. A compound as defined in claim 1, wherein Ar is selected from phenyl and pyrrol-1-yl groups substituted at both ortho-position carbon atoms of the group, each substituent being independently selected from halogen, lower alkyl and trifluoromethyl.

3. A compound as defined in claim 1 or 2, wherein $R_1$, $R_2$, $R_3$, $R_4$ and $R_5$ are each independently selected from hydrogen and methyl.

4. N-[Amino(cyanamino)methylene]-2,6-dichlorobenzeneacetamide.

5. A pharmaceutical composition comprising an antihypertensively effective amount of a compound as defined in claim 1 in association with a pharmacologically acceptable carrier.

6. A composition as defined in claim 5, which contains an effective amount of N-[Amino(cyanamino)methylene]-2,6-dichlorobenzeneacetamide.

7. A method of lowering blood pressure in a hypertensive subject, which comprises administering an effective amount of a compound as defined in claim 1.

8. A method as claimed in claim 7, wherein the compound administered is N-[Amino(cyanamino)methylene]-2,6-dichlorobenzeneacetamide.

* * * * *

UNITED STATES PATENT OFFICE
CERTIFICATE OF CORRECTION

Patent No. 4,332,822          Dated June 1, 1982

Inventor(s) Terence James Ward

It is certified that error appears in the above-identified patent and that said Letters Patent are hereby corrected as shown below:

Col. 2, line 65, "$Ar-CR_4R_5-CO-Cl$" should read --$Ar-CR_4R_5-CO_2H$--;

Col. 4, line 11, "$Ar-CR_4R_5-CO_2H$" should read --$Ar-CR_4R_5-CO-Cl$--.

Signed and Sealed this

Seventeenth Day of August 1982

[SEAL]

Attest:

GERALD J. MOSSINGHOFF

Attesting Officer      Commissioner of Patents and Trademarks